United States Patent
Shepard

[11] Patent Number: 4,738,673
[45] Date of Patent: Apr. 19, 1988

[54] CATHETER FOR DETECTING CALCULI

[76] Inventor: Barry Shepard, 46 Fortune La., Jericho, N.Y. 11753

[21] Appl. No.: 12,792

[22] Filed: Feb. 9, 1987

[51] Int. Cl.[4] .............................................. A61M 1/00
[52] U.S. Cl. .................................... 604/327; 604/349; 128/328
[58] Field of Search .............. 128/328; 604/327–332, 604/347–353

[56] References Cited

U.S. PATENT DOCUMENTS 1,643,631  9/1927  Schulz ................................. 128/328
2,789,560  4/1957  Weimer .............................. 604/349

FOREIGN PATENT DOCUMENTS 641521  9/1927  France .................................. 604/349

Primary Examiner—C. Fred Rosenbaum
Assistant Examiner—J. L. Kruter

[57] ABSTRACT

An elastomeric tubular sheath is secured over the user's penis having an operative end in a forwardly spaced position. A strainer is provided at the forward end having filtering means with openings sized to retain calculi but to otherwise allow the passage of urine therethrough.

2 Claims, 1 Drawing Sheet

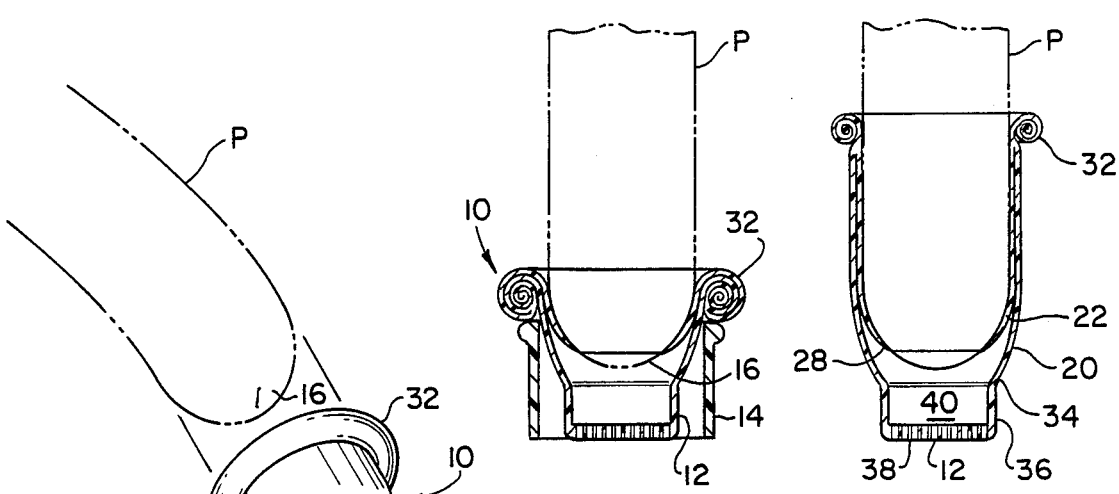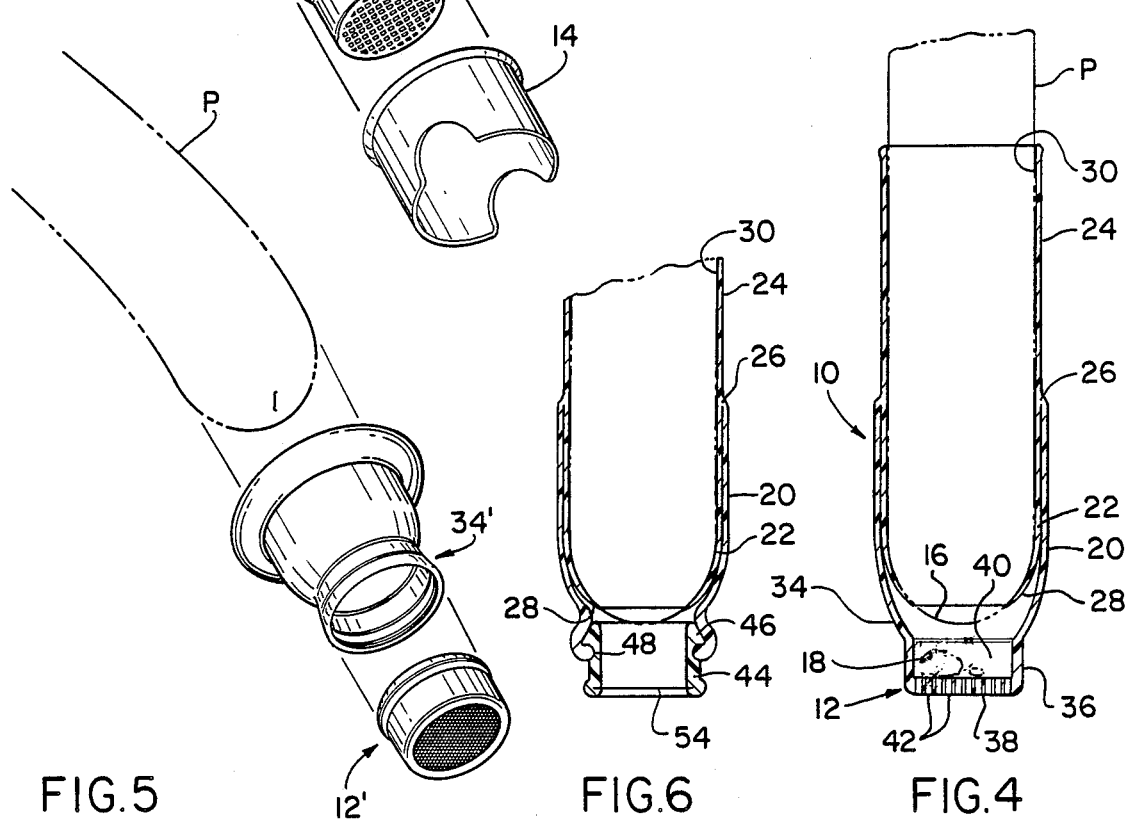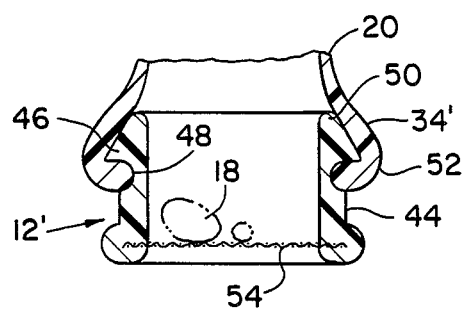

CATHETER FOR DETECTING CALCULI

BACKGROUND OF THE INVENTION

The present invention relates to a system for collecting calculi passing in the urine of male patients.

The collection of calculi, i.e., urinary stones presents some difficulty to otherwise fully mobile and ambulatory males. At present, the patient must carry with him a supply of filter paper which he must hold in his hands whenever he urinates allowing the fluid to flow through and the calculi to be captured by the paper. Should a stone be passed during urination, the patient must first remove it from the filter paper and store it in a vial or the like for further examination and testing by the physician. In any event, the filter paper must be discarded once used, raising some sanitary problems and annoyance to the patient. Since the condition requiring collection of calculi, also requires the patient to urinate a great number of times during the day, the present system is not only cumbersome but is also highly inconvenient.

It is an object of the present invention to provide a simplified system for collecting calculi from the urine, which is more sanitary and more convenient than heretofore known.

These objects together with other objects and advantages are set forth in the following disclosure of the invention.

SUMMARY OF THE INVENTION

According to the present invention, a urinary tract calculi collection system is provided comprising an elastomeric tubular sheath adapted to be secured over and encircling the user's penis and having an operative end in a forwardly spaced position for impingement of the urine thereagainst. The operative end is provided with a strainer device having filtering means with size openings adapted to retain calculi but to otherwise allow the passage of urine therethrough at substantially the exiting pressure from the penis; the strainer device being also suitable to store the calculi until it is more convenient to remove them.

Full details of the present invention are set forth in the following description and are illustrated in the accompanying drawings.

BRIEF DESCRIPTION OF THE DRAWINGS

In the drawings;
FIG. 1 is a perspective view of the first embodiment of the calculi collection system of the present invention,
FIG. 2 is a sectional view showing the device in the initial position for application to the penis,
FIG. 3 is a sectional view showing the device in an intermediate position during application to the penis,
FIG. 4 is a sectional view showing the final position of the device applied to the penis,
FIG. 5 is a perspective view of a second embodiment of the present invention,
FIG. 6 is a sectional view of the device shown in FIG. 5 as fully applied to the penis,
FIG. 7 is an enlarged cross-sectional view of the lower end of the embodiment shown in FIGS. 5-6.

DESCRIPTION OF THE INVENTION

In the embodiment shown in FIGS. 1-4, the urinary tract calculi collection system of the present invention comprises, an elastomeric coupling sheath 10 for application about the penis P and a cup shaped strainer 12 integraly attached thereto, through which the urine is to pass.

The coupling sheath 10 is adapted to be secured on the end of the penis P, using, if desired, an applicator ring 14, so that the strainer 12, spaced from the tip 16 of the penis, permits, as will be described later, free flow of urine, at a rate substantially equal to the exiting rate from the penis but retention of any calculi 18 contained therein. As seen in full extension in FIG. 4, the sheath 10 comprises an outer sleeve 20 and a concentric inner sleeve 22, which merge into a single wall 24 at their proximal ends 26 (with respect to the user). At the distal or operative of the sheath end, the inner sleeve 22 is provided with a convex flap 28 adapted to abut against the glans penis but leave the tip 16 of the penis P free to protrude partially therethrough so as not to cause any interference with urination. The inner surface of the single wall 24, as seen in FIG. 2, is provided with a tenacious adhesive layer 30 capable of holding fast to the dermal surface of the penis P.

As seen in FIG. 2, the sheath 10 is normally provided for marketing, so that its single wall 24 and its adjacent inner and outer sleeves 20 and 22 are rolled on themselves as at 32. The roll 32 thus encloses the adhesive layer 30, so that during packaging and shipping, damage to the adhesive layer cannot occur. Further, the rolling of sheath 10 facilitates the ultimate placement of the device on the penis, as will be obvious from FIGS. 2-4, by simply placing the convex inner flap 28 against the glans penis and unrolling the sleeves and wall until the sheath fully encompasses the penis. The applicator ring 14 may be used since when placed over the sheath it will cause the roll 32 to unroll without need for the user's fingers to touch the adhesive layer.

In the embodiment detailed in FIGS. 1-4, the strainer 12 is integrally formed with the distal end 34 of the outer sleeve 20, preferably by integrally molding the sheath 10 and strainer 12 simultaneously. The strainer 12 is cup shaped, having a cylindrical wall 36 and a fenestrated end wall 38 spaced from and opposite the penis tip 16 so as to form a chamber 40 in which the calculi 18 can come to rest. The cylindrical wall 36 and the fenestrated end wall 38 of the strainer 12 are preferably semi-rigid, although also made of the same elastomeric material as the sheath 10, so that the strainer 12 will neither collapse nor the chamber 40 so defined, distort during wearing.

The fenestrated wall 38 is provided with holes 42 arranged over its entire area which are of such a size and number as to permit urine to flow freely, as the wearer urinates, even with the retention of some calculi within the strainer. In general, the urine flow is at a rate of between 20-50 ccs per second. Thus the number of holes 42 and their size can be easily determined to permit the flow through the strainer at that rate or at any other predetermined rate without backup whatsoever. Further, the size of the holes 42 themselves can be predetermined so as to retain calculi of any desired size. The system permits the urine exiting at its normal pressure, to pass through the filter of the strainer at the exiting pressure which acts to contribute to the filtration action rather than the inflation of the elastomeric sheath with fluid.

The coupling sheath 10 and the strainer 12 are preferably formed of a surgical grade elastomeric material, as rubber, plastic or the like, and of a thickness to permit easy manipulation and retention on the penis. The semirigidity of the strainer and sheath at the forward portion 34 can be obtained by thickening the wall without the need for any embedded structural reinforcement. The adhesive used in the layer 30 to hold the coupling sheath on the penis can be selected from any one of the conventionally used body adhesives and in particular, from those adhesives currently available to secure external penal catheters.

In removing the device from the penis, the coupling sheath is merely rerolled from the proximal end to the distal end, in reverse to its application onto the penis. The removal of accumulated calculi, from within the strainer cup 12, can be easily made through the inner flap 28 or the strainer cup 12 may be cut from the coupling sheath 10. Most likely the latter procedure would be most convenient as the device itself will be discarded, in any event, after each use.

The embodiment illustrated in FIGS. 5–7 is basically similar to the device described in connection with FIGS. 1–4 (the same parts bearing the same reference numbers). Here however, a basket type strainer, generally designated by the numeral 12' is provided separably from the coupling sheath 10 so that it may be removed independently and without removing the sheath itself from the penis. To this end, the basket strainer 12' comprises a semi-rigid cylindrical section 44 having an annular collar 46 and a groove 48 near its proximal end 50. The outer sleeve 20 is provided with a terminal end 34' which is semi-rigid, but which is provided with an inwardly directed lip 52 adapted to be snapped over the collar 46 to seat within the groove 48. The basket strainer 12' is completed by imbedding a sheet of mesh filter material 54, such as nylon or metal screening, by its circumferential edge within the wall of the cylindrical section 44. The basket strainer 12' may thus be easily removed when its contents are to be inspected and replaced or substituted with another basket if desired, all without removal of the sheath 10 from the penis.

It will be clearly observed from the foregoing, that the present invention provides a system whereby mobile male patients could apply the device, say in the morning, and use it several times during the day, without its removal, and then examine the strainer for solids such as the calculi in the evening. The device is preferably made of translucent rubber or clear flexible plastic so that its interior can be readily observable. Thus, the patient will not only know that he has passed calculi, but will also be able to observe the accumulation within the device.

Further, the patient will experience no discomfort from the device, nor will the device interfere with normal urination. Neither, will the patient suffer embarrassment because of the need to carry paper filters, containers, etc. and from the need to dispose of them in a sanitary way. In the alternate embodiment of FIGS. 5–7 the separable basket strainer enables the calculi to be properly removed from the device more frequently than once a day without the removal of the sheath. A clean basket may then be substituted for the next use. This enables prompt and ready examination of the calculi without the need for destroying the device itself.

The foregoing description has set forth several embodiments and modifications. Other changes, modifications and embodiments will be obvious to those skilled in the art. Accordingly, it is intended that the present disclosure be taken as illustrative only and not limiting of the scope of the present invention.

What is claimed is:

1. A urinary tract calculi collection system comprising an elastomeric tubular sheath adapted to be secured over and encircle the user's penis and having an operative end formed as a semi-rigid substantially cylindrical wall in a spaced position forwardly of the tip of the penis and a strainer consisting of a mesh screen embedded at its periphery in said cylindrical wall having openings sized to retain calculi but ot otherwise allow the passage of urine therethrough mounted at operative end of said sheath, said strainer being suitable to store the calculi until it is more convenient to remove them, said semi-rigid cylindrical wall and said strainer being provided with cooperating detent and groove means for removably securing said strainer to said sheath.

2. A urinary tract calculi collection system comprising an elastomeric tubular adapted to be secured over and encircle the user's penis and having an operative end in a spaced position forwardly of the tip of the penis and a strainer consisting of a semi-rigid elastomeric cup having a cylindrical side wall and a fenestrated end wall, said fenestrated end wall being formed integrally with said side wall and being provided with an array of holes having a predetermined size suficient in toto to allow urine to flow therethrough at a rate substantially equivalent to the rate of normal existing flow from the user.

* * * * *